(12) United States Patent
Sugiyama et al.

(10) Patent No.: US 9,539,299 B2
(45) Date of Patent: Jan. 10, 2017

(54) COMBINATION THERAPY WITH WT1 PEPTIDE VACCINE AND TEMOZOLOMIDE

(71) Applicant: INTERNATIONAL INSTITUTE OF CANCER IMMUNOLOGY, INC., Suita (JP)

(72) Inventors: Haruo Sugiyama, Mino (JP); Toshiki Yoshimine, Ashiya (JP); Akihiro Tsuboi, Osaka (JP); Naoya Hashimoto, Mino (JP)

(73) Assignee: International Institute of Cancer Immunology, Inc., Suita (JP)

( * ) Notice: Subject to any disclaimer, the term of this patent is extended or adjusted under 35 U.S.C. 154(b) by 0 days.

(21) Appl. No.: 13/665,597

(22) Filed: Oct. 31, 2012

(65) Prior Publication Data

US 2013/0225502 A1     Aug. 29, 2013

Related U.S. Application Data

(60) Provisional application No. 61/552,209, filed on Oct. 27, 2011.

(51) Int. Cl.
    *C07K 14/00*     (2006.01)
    *A61K 38/08*     (2006.01)
    *A61K 31/495*     (2006.01)

(52) U.S. Cl.
    CPC ............ *A61K 38/08* (2013.01); *A61K 31/495* (2013.01)

(58) Field of Classification Search
None
See application file for complete search history.

(56) References Cited

U.S. PATENT DOCUMENTS

| | | | |
|---|---|---|---|
| 5,939,098 A * | 8/1999 | Reidenberg et al. | 424/451 |
| 7,030,212 B1 * | 4/2006 | Sugiyama et al. | 530/328 |
| 7,488,718 B2 * | 2/2009 | Scheinberg et al. | 514/1.1 |
| 7,939,627 B2 * | 5/2011 | Nishihara et al. | 530/328 |
| 8,105,604 B2 * | 1/2012 | Sugiyama | 424/185.1 |
| 8,388,975 B2 * | 3/2013 | Sugiyama | 424/185.1 |
| 2010/0190163 A1 | 7/2010 | Sugiyama | |

FOREIGN PATENT DOCUMENTS

WO     2007/063903     * 6/2007

OTHER PUBLICATIONS

Johnson et al, Cancer Treatment Reviews vol. 2 p. 1 (1975).*
Gabrilovich, Lancer Oncology vol. 8 p. 2 (2007).*
U.S. Appl. No. 13/755,185, filed Jan. 31, 2012, Sugiyama.
Clinical trial plan dated Apr. 19, 2010.
Abstract of the 48th Annual Meeting of Japan Society of Clinical Oncology dated Oct. 28, 2010 [S30-7, PD16-1, PD16-4] with English translation, Declaration and Abstract.

* cited by examiner

*Primary Examiner* — Sheela J Huff
(74) *Attorney, Agent, or Firm* — Oblon, McClelland, Maier & Neustadt, L.L.P.

(57) ABSTRACT

The present invention relates to combination therapy for cancer with a WT1 peptide vaccine and temozolomide.

4 Claims, 1 Drawing Sheet

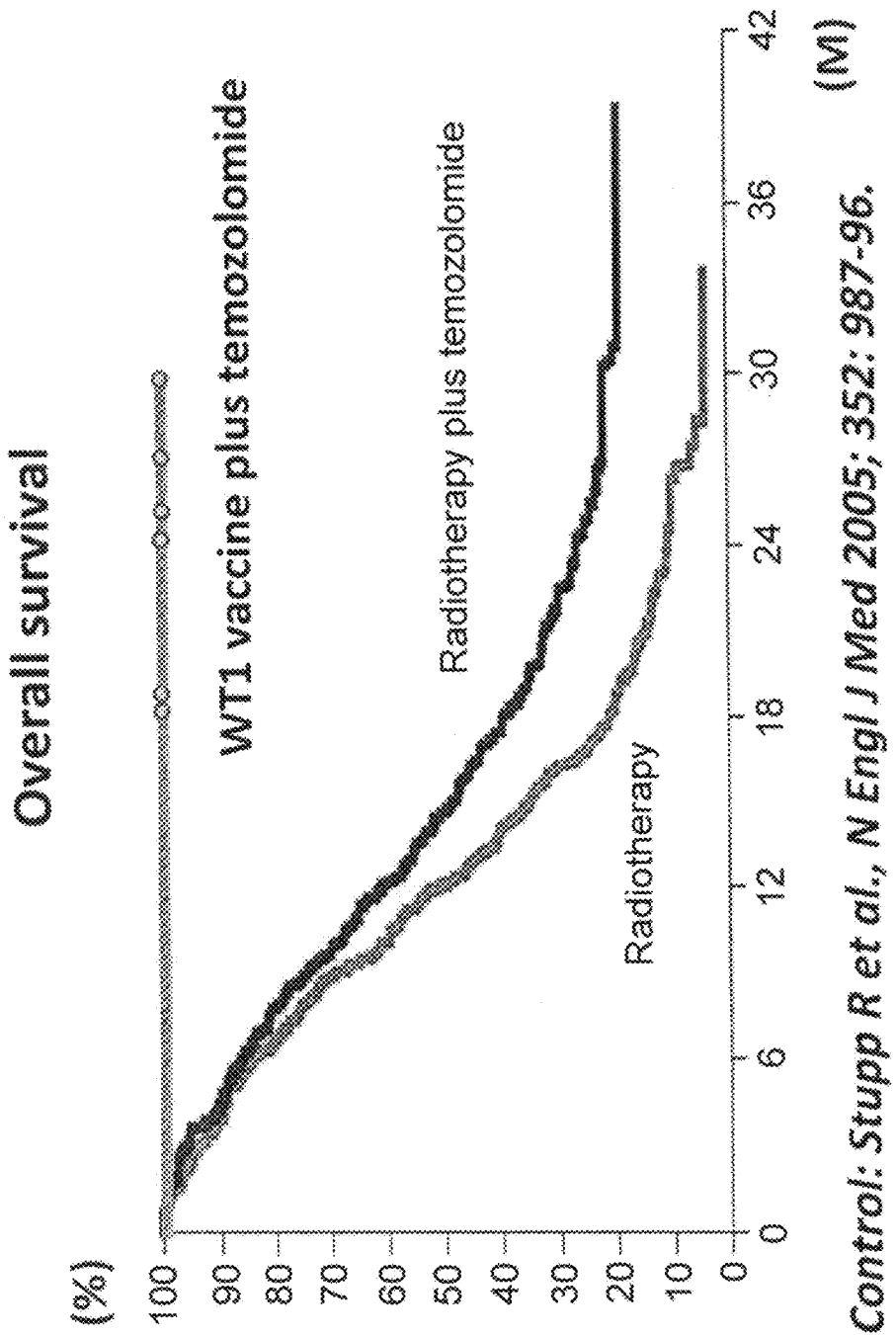

```
                        SEQUENCE LISTING

<160> NUMBER OF SEQ ID NOS: 6

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60

Pro Pro Pro Pro His Ser Phe Ile Lys Gln Glu Pro Ser Trp Gly Gly
65                  70                  75                  80
```

Ala Glu Pro His Glu Gln Cys Leu Ser Ala Phe Thr Val His Phe
            85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
            210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
            370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Cys Tyr Thr Trp Asn Gln Met Asn Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Arg Met Phe Pro Asn Ala Pro Tyr Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Tyr Met Phe Pro Asn Ala Pro Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Ser Leu Gly Glu Gln Gln Tyr Ser Val
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-terminal Cys residue is bonded to a second
      Cys via a disulfide bond, where the second Cys is not peptide
      bonded to the compound

<400> SEQUENCE: 6

Cys Tyr Thr Trp Asn Gln Met Asn Leu
1               5

COMBINATION THERAPY WITH WT1 PEPTIDE VACCINE AND TEMOZOLOMIDE

CROSS-REFERENCE TO RELATED APPLICATIONS

This application claims priority based on U.S. Provisional Application No. 61/552,209, filed Oct. 27, 2011 (incorporated herein by reference in its entirety).

BACKGROUND OF THE INVENTION

Field of the Invention

The present invention relates to combination therapy for cancer with a WT1 peptide vaccine and temozolomide. The present invention also relates to a pharmaceutical composition comprising a WT1 peptide, characterized by being used in combination with temozolomide.

Background Art

WT1 gene (Wilms' tumor 1 gene) is a gene identified as a causative gene for Wilms' tumor that is a childhood renal cancer, and encodes a transcription factor having a zinc finger structure. WT1 gene was initially considered to be a tumor suppressor gene. However, subsequent studies revealed that it rather functioned as an oncogene in a hematopoietic organ tumor and a solid cancer.

It has been shown that the in vitro stimulation of peripheral blood mononuclear cells with a WT1 peptide induces cytotoxic T-lymphocytes (CTLs) specific for the peptide, which kill hematopoietic organ tumor or solid cancer cells endogenously expressing WT1. Various WT 1 peptides capable of inducing WT1-specific CTLs, which are expected to be used for cancer immunotherapy, have previously been identified (Patent Literatures 1 to 11). Phase I and phase II clinical trials for cancer immunotherapy using WT1 peptides have also been conducted (Non Patent Literatures 1 to 4).

The presence of helper T cells specific for a cancer antigen is reported to be important for the efficient induction of CTLs. Helper T cells are induced and activated by recognizing a complex of an MHC class II molecule in antigen-presenting cells and an antigen peptide to thereby promote the proliferation, differentiation, and maturation of B cells and subsets of other T cells. Therefore, it is considered to be useful in cancer immunotherapy to activate the immune system through the induction of helper T cells by an antigen peptide that binds to an MHC class II molecule; a plurality of WT1 peptides having such a function have also previously been reported (Patent Literatures 12 to 14 and Non Patent Literature 5).

Gliomas are primary brain tumors arise from glial cells. What are considered to be malignant among gliomas are glioblastoma and anaplastic astrocytoma, and glioblastoma is a tumor occurring most frequently and having high malignancy among primary brain tumors and is a poor-prognosis disease having a life expectancy of 12 to 14 months and a 5-year survival of 5%. Surgery is the first choice for the treatment of newly-diagnosed malignant glioma; however, it is standard therapy therefor to perform radiation therapy and the administration of temozolomide as a chemotherapeutic agent against postoperative residual tumor cells because the glioma shows a marked tendency for invasion and is difficult to completely remove. However, its therapeutic results are not satisfactory with a median overall survival (OS) of 14.6 months, a median progression-free survival (PFS) of 6.9 months, and a median 2-year survival of 26% (Non Patent Literature 6).

Most chemotherapeutic agents nonspecifically affect not only tumor cells but also normal cells at a proliferative phase, and lymphocytes proliferated and activated by antigen stimulation are also similarly affected. Therefore, the immune system of a patient receiving chemotherapy is considered to be suppressed; regarding the simultaneous combined use of chemotherapy and immunotherapy, concerns exist about deleterious effects of chemotherapy on CTLs, i.e., cell-killing effects on CTLs in addition to the same effects on cancer cells. No therapy involving the combined use of cancer peptide vaccine therapy and temozolomide has previously been reported.

CITATION LIST

Patent Literature

[Patent Literature 1] International Publication No. WO 2000/006602
[Patent Literature 2] International Publication No. WO 2002/079253
[Patent Literature 3] International Publication No. WO 2003/106682
[Patent Literature 4] International Publication No. WO 2004/026897
[Patent Literature 5] International Publication No. WO 2004/063217
[Patent Literature 6] International Publication No. WO 2005/095598
[Patent Literature 7] International Publication No. WO 2007/097358
[Patent Literature 8] International Publication No. WO 2008/081701
[Patent Literature 9] International Publication No. WO 2009/072610
[Patent Literature 10] International Publication No. WO 2007/063903
[Patent Literature 11] International Publication No. WO 2000/018795
[Patent Literature 12] International Publication No. WO 2008/105462
[Patent Literature 13] International Publication No. WO 2010/123065
[Patent Literature 14] International Publication No. WO 2005/045027

Non Patent Literature

[Non Patent Literature 1] Proc. Natl. Acad. Sci. USA, 2004; 101(38): 13885-90
[Non Patent Literature 2] Int. J. Hematol., 2003; 78(1): 56-61
[Non Patent Literature 3] Jpn. J. Clin. Oncol., 2006 April; 36(4): 231-6
[Non Patent Literature 4] J. Neurosurg., 2008 May; 108 (5): 963-71
[Non Patent Literature 5] Cancer. Immunol. Immunother., 51:271, 2002
[Non Patent Literature 6] N. Engl. J. Med., 2005 Mar. 10; 352 (10): 987-96

The above literatures are incorporated herein by reference.

BRIEF SUMMARY OF THE INVENTION

An object of the present invention is to provide a more effective method for treating cancer using a WT1 peptide vaccine.

The present inventor has found that chemotherapy with temozolomide is used in combination with WT1 peptide vaccine therapy in malignant glioma patients after extirpative surgery for tumor to provide an effective anti-tumor effect and prolong survival, thereby accomplishing the present invention.

Thus, the present invention provides a method for treating cancer, comprising administering therapeutically effective doses of a WT1 peptide and temozolomide to a patient in need thereof.

The present invention also provides a pharmaceutical composition comprising a WT1 peptide for treating cancer, wherein the composition is used in combination with temozolomide. The present invention further provides a pharmaceutical composition comprising temozolomide for treating cancer, wherein the composition is used in combination with a WT1 peptide.

The present invention also provides a kit for treating cancer, comprising a WT1 peptide and temozolomide.

The present invention also provides use of a WT1 peptide for treating cancer, wherein the WT1 peptide is used in combination with temozolomide.

According to the present invention, the combination of cancer immunotherapy targeting WT1 with chemotherapy using temozolomide enables more effective therapy of cancer than WT1 alone or temozolomide alone.

BRIEF DESCRIPTION OF THE DRAWING

FIG. 1 shows a comparison between the total survival of patients given only radiation therapy or only a combination therapy of radiation therapy and temozolomide as reported in N. Engl. J. Med., 2005; 352: 987-996 and the total survival of the patients given the combination therapy of the WT1 peptide vaccine of the present invention and temozolomide

DESCRIPTION OF EMBODIMENTS

The present invention relates to a method for treating cancer, comprising administering therapeutically effective doses of a WT1 peptide and temozolomide to a patient in need thereof.

The method of the present invention is characterized in that cancer immunotherapy with a WT1 peptide vaccine that induces or potentiates the killing of WT1-expressing cancer cells is used in combination with temozolomide as a chemotherapeutic agent. The WT1 peptide according to the present invention may be a peptide capable of binding to an MHC class I molecule to induce antigen-specific CTLs (hereinafter, referred to as a CTL peptide), or a peptide capable of binding to an MHC class II molecule to induce antigen-specific helper T cells (hereinafter, referred to as a helper peptide).

Specifically, the WT1 peptide of the present invention is a peptide consisting of a portion of the amino acid sequence of human WT1 protein shown in SEQ ID NO: 1, capable of binding to an MHC class I molecule to induce WT1-specific CTLs (i.e., having a function as the CTL peptide), or a peptide consisting of an amino acid sequence in which one or several, preferably one or two amino acids are substituted, deleted, and/or added in the amino acid sequence of the above peptide, having a function as the CTL peptide. The WT1 peptide may also be a peptide consisting of a portion of the amino acid sequence of human WT1 protein of SEQ ID NO: 1, capable of binding to an MHC class II molecule to induce WT1-specific helper T cells (i.e., having a function as the helper peptide), or a peptide consisting of an amino acid sequence in which one or several, preferably one or two amino acids are substituted, deleted, and/or added in the amino acid sequence of the above peptide, having a function as the helper peptide.

The WT1 peptide is not particularly limited in the amino acid sequence and length thereof provided that it has the above characteristics. The CTL peptide preferably consists of 6 to 30 amino acids, more preferably 7 to 20 amino acids, still more preferably 8 to 12 amino acids, for example, 8, 9, 10, or 11 amino acids, considering binding properties to the MHC class I molecule. The helper peptide preferably consists of 10 to 25 amino acids, more preferably 15 to 21 amino acids, still more preferably 16 to 20, for example, 17, 18, or 19 amino acids, considering binding properties to the MHC class II molecule.

The MHC class I molecule to which the peptide of the present invention binds may be any subtype thereof, and examples thereof include HLA-A02, HLA-A11, HLA-A24, HLA-A26, and HLA-A33. The MHC class II molecule to which the peptide of the present invention binds may also be any of the subtypes of HLA-DR, HLA-DQ, and HLA-DP.

The amino acid substitution may be performed between any amino acids at any position in the amino acid sequence of the peptide; however, it is preferably a conservative amino acid substitution. For example, it is preferable to substitute an Asp residue for a Glu residue, a Tyr residue for a Phe residue, a Ile residue for a Leu residue, a Ser residue for Ala residue, or an Arg residue for a His residue. The addition and deletion of an amino acid may be performed at any positions; however, they are preferably performed at the N terminal end and C terminal end of the peptide.

When the sequence regularities (motifs) of the antigen peptide binding to the MHC class I and class II molecules are revealed, the amino acid substitution is preferably performed based on the motifs. For example, in the case of HLA-A24, it is known that the amino acid at the second position of a peptide consisting of 8 to 11 amino acids is tyrosine, phenylalanine, methionine, or tryptophan and the C-terminal end thereof is phenylalanine, leucine, isoleucine, tryptophan, or methionine (J. Immunol., 152, p 3913, 1994; Immunogenetics, 41: p 178, 1995, J. Immunol., 155: p 4307, 1994) (both are incorporated herein by reference). Thus, in the case of a HLA-24-binding peptide, amino acids at the second position and/or at the C-terminal end are preferably substituted with amino acids within the above-described range. This is ditto for other subtypes of the MHC class I and class II molecules such as HLA-A2 (Immunogenetics, 41, p 178, 1995; J. Immunol., 155: p 4749, 1995) (both are incorporated herein by reference) and HLA-DRB1*0405 (Immunogenetics, 41, 178-228 (1995); Biochimica et Biophysica Acta 1316, 85-101, 1996) (both are incorporated herein by reference).

The amino acid sequences of peptides predicted to be capable of binding to MHC class I and class II molecules can be searched using BIMAS software of NIH on the Internet, BIMAS HLA peptide binding prediction analysis (J. Immunol., 152, 163, 1994), the MHC class II-binding sequence prediction program, ProPred, on the Internet (Bioinformatics 17: 1236, 2001), or the like.

The W1 peptide may have one or a plurality of modified amino acid residues. Examples of the modification include the esterification, alkylation, halogenation, phosphorylation, sulfonation, and amidation of an amino acid residue. The WT1 peptide may also be modified by condensing a thiol group of a cysteine residue and a thiol group of cysteine, glutathione, thioglycolic acid, or the like, in the peptide via disulfide bonding (see International Publication No. WO 2007/063903 (incorporated herein by reference)). In addition, the WT peptide may be used in the form of a peptide dimer in which two monomers of the peptide are bonded together via disulfide bonding between the thiol groups of at least one pair of cysteine residues between the two monomers (see International Publication No. WO 2004/063217

(incorporated herein by reference)). The amino acids constituting the WT1 peptide may be natural occurring amino acids or synthetic amino acids. Such peptide modification is only illustrative, and the peptides modified by methods known in the art can be all used in the present invention.

The WT1 peptide can be synthesized by methods usually used in the art or modifications thereof. Such synthesis methods are described, for example, in Peptide Synthesis, Interscience, New York, 1966; The Proteins, Vol. 2, Academic Press Inc., Newyork, 1976; "Pepuchido Gosei (Peptide Synthesis)", Maruzen Co., Ltd., 1975; Pepuchido Gosei No Kiso To Jikken (Basis and Experiment for Peptide Synthesis) published by Maruzen Co., Ltd., 1985; and "Pepuchido Gosei (Peptide Synthesis)", Iyakuhin No Kaihatsu Zoku (Development of Pharmaceutical Product (Continued)) vol. 14, published by Hirokawa Shoten, 1991 (all are incorporated herein by reference). The WT1 peptide can also be produced using genetic engineering procedures on the basis of the information of the nucleotide sequence encoding the peptide. Such genetic engineering procedures are well known to those skilled in the art and are described, for example, in Molecular Cloning, T. Maniatis et al., CSH Laboratory (1983); DNA Cloning, D M. Glover, IRL PRESS (1985) (both are incorporated herein by reference).

Whether the peptide has a function as the CTL peptide can be examined by a method as described, for example, in J. Immunol., 154, p 2257, 1995 (incorporated herein by reference). Specifically, when peripheral blood mononuclear cells are isolated from an HLA antigen-positive human and stimulated by adding a candidate peptide in vitro, CTLs specifically recognizing HLA-positive cells pulsed with the peptide can be induced to confirm that the peptide has antigen-specific T cell-inducing activity. Here, the presence of CTL induction can be examined, for example, by measuring the amount of IFN-γ produced by CTLs in response to antigen-presenting cells presenting the peptide by an enzyme-linked immunosorbent assay (ELISA). The examination can also be carried out by measuring the amount of TNF-α produced by CTLs in response to antigen-presenting cells, based on the survival rate of a TNF-α-sensitive cell line (for example, WEHI164S cells; ATCC No. CRL-1751). In addition, the examination can also be performed by a method for measuring the killing property of CTLs against antigen-presenting cells labeled with $^{51}$Cr ($^{51}$Cr release assay, Int. J. Cancer, 58: p 317, 1994 (incorporated herein by reference)). The examination can also be examined by pulsing cells in which an expression plasmid capable of expressing cDNA for HLA is introduced e.g., into COS-7 cells (ATCC No. CRL1651) or VA-13 cells (Riken Cell Bank), with a candidate peptide, reacting these cells with the CTLs prepared above and the like, and measuring the amount of various cytokines (e.g., IFN-γ and TNF-α) produced by the CTLs.

Whether the peptide has a function as the helper peptide can be examined by a known method as described in Cancer Immunol. Immunother. 51:271, 2002 (incorporated herein by reference) or the like. For example, dendritic cells (adherent cells) are prepared by recovering peripheral blood mononuclear cells from an HLA antigen-positive human and removing floating cells therefrom. Separately, helper T cells (CD4-positive T cells) are prepared from the same HLA antigen-positive human by a Ficoll-Paque density gradient centrifugation method. Then, a candidate peptide is added to the above-described dendritic cells, which is then cultured, followed by mix-culturing the dendritic cells and the above-described helper T cells. Thereafter, the helper T cells are recovered and stimulated a number of times with the dendritic cells pulsed with the candidate peptide. The induction (activation) of helper T cells in response to the peptide stimulation can be examined, for example, by measuring (1) the growth activity of helper T cells or (2) the cytokine-producing-activity of helper T cells. The growth activity in (1) can be examined by measuring the amount of [$^3$]-thymidine incorporated into the helper T cells. The cytokine-producing-activity in (2) can be examined by measuring the amount of cytokines such as IFN-γ produced by activated helper T cells by ELISA or the like.

Examples of the WTI peptide suitable for the present invention include WT1 peptides as described in the following references: International Publication No. WO 2000/006602 International Publication No. WO 2002/079253; International Publication No. WO 2003/106682; International Publication No. WO 2004/026897; International Publication No. WO 2004/063217; International Publication No. WO 2005/095598; International Publication No. WO2007/097358; International Publication No. WO2008/081701; International Publication No. WO2009/072610; International Publication No. WO2007/063903; International Publication No. WO 2000/018795; International Publication No. WO 2008/105462; International Publication No. WO 2010/123065; International Publication No. WO 2005/045027; Cancer, Immunol. Immunother. 51:271, 2002 (Patent Literatures 1 to 13 and Non Patent Literature 5); International Publication No. WO 2003/002142; International Publication No. WO 2003/022757; International Publication No. WO 2003/028758; U.S. Pat. No. 7,030,212; U.S. Patent Application Publication No. 2004/097703; U.S. Patent Application Publication No. 2007/082860; U.S. Patent Application Publication No. 2006/205667; U.S. Patent Application Publication No. 2006/217297; U.S. Patent Application Publication No. 2008/152631; U.S. Patent Application Publication No. 2010/292160; U.S. Patent Application Publication No. 2011/098233; U.S. Patent Application Publication No. 2011/070251; U.S. Patent Application Publication No. 2010/062010; U.S. Pat. No. 7,063,854; U.S. Patent Application Publication No. 2010/247556; U.S. Patent Application Publication No. 2008/070835; U.S. Patent Application Publication No. 2006/165708; U.S. Patent Application Publication No. 2004/247609; U.S. Patent Application Publication No. 2005/002951 (all are incorporated herein by reference).

Among others, preferred is a peptide selected from the group consisting of:
Cys Tyr Thr Trp Asn Gln Met Asn Leu (SEQ ID NO. 2);
Avg Met Phe Pro Asn Ala Pro Tyr Leu (SEQ ID NO. 3);
Tyr Met Phe Pro Asn Ala Pro Tyr Leu (SEQ ID NO. 4);
Ser Leu Gly Glu Gln Gln Tyr Ser Val (SEQ ID NO. 5); and

[Formula 1]

(SEQ ID NO:6)

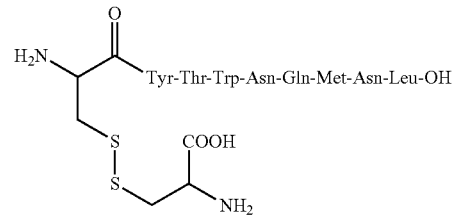

A peptide may be used which consists of an amino acid sequence in which one or several, preferably one or two amino acids are substituted, deleted, and/or added in the amino acid sequence of each of these peptides and has an function as the CTL peptide or the helper peptide.

The dose of the WT1 peptide is properly varied depending on the age and sex of a patient, the severity of disease, and the like; however, it is typically 0.0001 mg to 1,000 mg, preferably 0.01 mg to 100 mg, more preferably 0.01 mg to 10 mg, for example 1, 2, 3, or 5 mg per administration.

Examples of the dosage form suitable for the administration of the WT1 peptide include a water-in-oil (w/o) emulsion, an oil-in-water (o/w) emulsion, a water-in-oil-in-water (w/o/w) emulsion, a liposome formulation, a microsphere formulation, a microencapsulated formulation, a solid injection, or a liquid formulation. These formulations may be lyophilized formulations. The formulation may contain, as needed, a stabilizer (for example, a polysaccharide, an amino acid, a protein, urea, or sodium chloride), an excipient (for example, a saccharide, an amino acid, urea, or sodium chloride), an antioxidant, a preservative, an isotonizing agent, or a buffering agent. The formulation for administering the WT1 peptide may be formulated in advance or may be prepared at the time of use in administration to a patient. The WT1 peptide may be administered together with an appropriate adjuvant or may be formulated together with an adjuvant.

Temozolomide is an anti-cancer agent as a monovalent alkylating agent, is non-enzymatically converted to methyldiazonium ion under conditions of physiological pH, and exhibits an anti-tumor effect by methylating DNA. According to the method of the present invention, the dosage form of temozolomide and the method of administration thereof are not particularly limited. Temozolomide is sold in the forms of capsules and intravenous drip infusions under the trade name "Temodar (R)" from Schering-Plough Corporation; according to the present invention, the capsule may be orally administered, or the injection may be intravenously administered. The dose of temozolomide is properly varied depending on the age and sex of a patient, the severity of disease, and the like; however, it is typically 50 to 300 mg/m$^2$ (body surface area), preferably 75 to 200 mg/m$^2$ (body surface area), for example, 75, 150, or 200 mg/m$^2$ (body surface area) on a once-daily basis.

The period and time of administration of the WT1 peptide and temozolomide are not particularly limited. The WT1 may be administered from before the administration of temozolomide, may be administered over the whole or partial period of administration of temozolomide, or may be administered after the administration of temozolomide. For example, in a standard therapy for newly-diagnosed glioma, temozolomide is orally administered at 75 mg/m$^2$ (body surface area)/administration once daily for continuous 42 days in combination with radiation irradiation as an after-treatment after extirpative surgery for tumor, followed by 4 weeks off treatment. Thereafter, temozolomide alone is orally given at 150 mg/m$^2$/administration once daily for continuous 5 days, followed by 23 days off treatment. The 28 days are defined as 1 course, and at the second course and later, temozolomide is orally given at 100, 150, or 200 mg/m$^2$/administration once daily for continuous 5 days, followed by 23 days off treatment. In this case, after the end of radiation therapy, the WT1 peptide may be administered for the same period as the period of administration of temozolomide, may be administered for a portion of the period of administration of temozolomide, may be continuously administered for a period including the duration of the off-treatment, or may be administered for a period other than the period of administration of temozolomide. The above treatment regimens are only illustrative, and the patient may receive or not receive other anticancer therapies including radiation therapy or extirpative surgery for tumor.

According to the present invention, the treatment of cancer includes both preventive treatment and therapeutic treatment. Examples of the treatment of cancer include the shrinkage or suppression of increase of tumor lesions, the suppression of appearance of new lesions, the prolongation of survival, the improvement or suppression of progression of subjective and objective symptoms associated with tumor, the suppression of metastasis, and the prevention of recurrence.

The method of the present invention can be used for the treatment of various cancers including hematopoietic organ tumors such as leukemia, myelodysplastic syndrome, multiple myeloma, and malignant lymphoma, and solid cancers such as glioma, stomach cancer, large bowel cancer, lung cancer, breast cancer, germ-cell cancer, liver cancer, skin cancer, bladder cancer, prostate cancer, uterine cancer, uterocervical cancer, and ovary cancer; however, it is particularly suitable for glioma.

The present invention also relates to: a pharmaceutical composition comprising a WT1 peptide for treating cancer, wherein the composition is used in combination with temozolomide; a kit for treating cancer, comprising a WT1 peptide and temozolomide; and the use of a WT1 peptide for treating cancer, wherein the WT1 peptide is used in combination with temozolomide. The dosage form, dose, and the like of the WT1 peptide and temozolomide for the pharmaceutical composition, kit, and use of the present invention are as described in the method for treating cancer.

The present invention will be specifically described below with reference to Examples. However, the present invention is not limited to these Examples in any sense.

EXAMPLE 1

1. Method

The phase I clinical trial of chemoimmunotherapy using temozolomide and a modified WT1 peptide (mp235-243) in combination as maintenance therapy after postoperative adjuvant chemoradiation therapy was performed in patients with newly-diagnosed malignant glioma.

(1) Test Agent
(i) WT1 Peptide Vaccine
Principal Ingredient: HLA-A*2402 restricted modified WT1 peptide (mp235-243): CYTWNQMNL (SEQ ID NO: 2)
Adjuvant: Montanide ISA 51 (250 µg/A): Freund's incomplete adjuvant
A saline solution of the WT1 peptide and Montanide ISA 51 were mixed at a weight ratio of 1:1 to prepare a water-in-oil emulsion, which was then used as a WT1 peptide vaccine.
(ii) Temozolomide
Trade Name: Temodar (R)" (Schering-Plough Corporation)
Dosage Form and Dose: Capsule 20 mg, 100 mg
(2) Patient
The patients were 5 HLA-A-2402 patients with glioblastoma and 1 HLA-A-2402 patient with anaplastic astrocytoma in whom WT1 gene was demonstrated to be expressed in the tumors.
(3) Treatment Regimen
As an after-treatment after extirpative surgery for tumor, 5-day/week 2 Gy radiation irradiation was performed once daily for 6 weeks and temozolomide (75 mg/m$^2$ once daily) was orally daily administered in irradiating radiation for 6 weeks as a rule (49 days at the longest). From the first to second weeks after the end of the radiation/temozolomide combination therapy, WT1 peptide vaccine therapy was started and the WT1 peptide vaccine (3 mg) was administered at intervals of 1 week. From the fourth week after the end of the radiation therapy, temozolomide (150 to 200 mg/m² once daily) was orally daily administered for 5 days. When the WT1 vaccine therapy was started from the first week after the end of the radiation/temozolomide combination therapy, the WT1 peptide vaccine was administered 3 times before the administration of maintenance temozolomide and 4 times from the time of the administration of maintenance temozolomide, 7 times in total. When the therapy was started at the second week, the number of times of administration was set to 6 in total.

(4) Evaluation (i) Tumor Response

The tumor response was evaluated using RECIST criteria. Tumor measurable by MRI as a rule was defined as a measurable lesion and had a maximum diameter of 10 mm or more in the case of a slice of 5 mm or less and a maximum diameter of 20 mm or more in the case of a slice of 5 mm to 10 mm (inclusive); however, it was determined as measurable if the maximum diameter was 2 times or more the slice width. Up to 5 of the measurable lesions observed before the start of administration in the order of decreasing the maximum diameter (hereinafter, referred to as the major diameter) were defined as target lesions, and lesions not chosen as the targets was all defined as non-target lesions irrespective of whether being measurable or not. Evaluation was performed within 2 weeks before the start of therapy by the administration of the WT1 peptide vaccine, every 4 weeks, as a rule, after the start thereof, and at the sixth week after the first administration of maintenance temozolomide.

(a) Response of Target Lesion

The response of target lesions was determined according to the following criteria.

TABLE 1

Response Evaluation Criteria for Target Lesion

| Classification | Definition |
|---|---|
| CR (Complete Response) | Disappearance of all target lesions including secondary changes due to tumor. |
| PR (Partial Response) | A 30% or more decrease in the sum of the major diameter of target lesions as compared to the sum of the major diameter thereof before treatment. |
| PD (Progression Disease) | A 20% or more increase in the sum of the major diameter of target lesions (including recurrence), compared to the smallest sum of the major diameter thereof previously observed. However, an increase in such a range that the absolute value of the sum of the major diameter thereof does not exceed 10 mm is not defined as PD. |
| SD (Stable Disease) | Neither tumor shrinkage to qualify for PR nor tumor increase to qualify for PD. |
| NE (Not Evaluable) | Incapability of examination for any reason, or incapability of determination as CR, PR, PD, or SD. |

Percentage of reduction of sum of major diameter=
(Sum of major diameter before therapy−Sum of major diameter at evaluation)/Sum of major diameter before therapy×100%

Percentage of increase of sum of major diameter=
(Sum of major diameter at evaluation−Smallest sum of major diameter)/Smallest sum of major diameter×100%

(b) Response of Non-Target Lesion

The response of non-target lesions was determined according to the following criteria.

TABLE 2

Response Evaluation Criteria for Non-Target Lesion

| Classification | Definition |
|---|---|
| CR | Disappearance of all non-target lesions. |
| IR/SD (Incomplete Response/Stable Disease) | No disappearance of one or more non-target lesions. |
| PD | Increase in non-target lesions (including reccurrence). |
| NE (Not Evaluable) | Incapability of examination for any reason, or incapability of determination as CR, IR/SD, or PD. |

(c) Overall Response

Overall response was determined according to the following from a tumor response for target lesions, a tumor response for non-target lesions, and the presence of appearance of a new lesion. When either target lesions or non-target lesions were determined to be NE, overall response was NE.

TABLE 3

Evaluation Criteria for Overall Response

| Response for Target Lesion | Response for Non-target Lesion | Presence of Appearance of New Lesion | Overall Response |
|---|---|---|---|
| CR | CR | No | CR |
| CR | IR/SD | No | PR |
| PR | Other Than PD | No | PR |
| SD | Other Than PD | No | SD |
| PD | Not Questioned | Not Questioned | PD |
| Not Questioned | PD | Not Questioned | PD |
| Not Questioned | Not Questioned | Yes | PD |

(d) Best Overall Response

Overall response was defined as "better" in the order of CR, PR, SD, PD, and NE, and best overall response was determined from overall responses for all courses according to the following criteria. When the best overall response corresponded to the definitions of a plurality of divisions, it was divided into a better one in the order of CR, PR, SD, PD, and NE.

TABLE 4

Evaluation Criteria for Best Overall Response

| Classification | Definition |
|---|---|
| CR | Resulting in an overall response of CR continuously 2 times or more at intervals of 4 weeks or more. |
| PR | Resulting in an overall response of PR or higher (CR or PR) continuously 2 times or more at intervals of 4 weeks or more. |
| SD | Resulting not in a best overall response of CR or PR but in the overall response being not PR at an interval of at least 12 weeks after the start of therapy and the overall response being SD or higher once or more. |

TABLE 4-continued

Evaluation Criteria for Best Overall Response

| Classification | Definition |
|---|---|
| PD | Resulting in an overall response of PD without corresponding to a best overall response of CR, PR, or SD. |
| NE | Resulting in an overall response of NE in all courses. |

(ii) Progression-Free Survival (PFS)

The day of surgery was used as the initial date of reckoning, and the period therefrom to the earlier date on which the disease was determined to have progressed and the date of death due to any cause was defined as progression-free survival (PFS).

2. Result

The results of evaluating the 6 patients are shown below.

TABLE 5

| Case | Age/Sex | Disease Name | Response | PFS (weeks) | OS (weeks) |
|---|---|---|---|---|---|
| 1 | 42/Male | Glioblastoma | CR | >84.6 | >84.6 |
| 2 | 55/Female | Glioblastoma | CR | >70.0 | >70.0 |
| 3 | 48/Male | Anaplastic Astrocytoma | CR | >64.7 | >64.7 |
| 4 | 41/Male | Glioblastoma | CR | >56.4 | >56.4 |
| 5 | 45/Male | Glioblastoma | CR | >33.0 | >33.0 |
| 6 | 60/Male | Glioblastoma | PD | 12.0 | >33.0 |

PFS: Progression-free survival
OS: Total survival

In 5 of the 6 tested patients, the evaluation of CR (complete response) was obtained and PFS (progression-free survival) was 30 weeks or more; in 4 patients, PFS was as long period as 50 weeks or more.

EXAMPLE 2

In patients 1 and 3, therapy by the administration of the WT1 peptide vaccine (3 mg, once per month) was continued, and in patients 2, 4, and 5, therapy was continued in which 1 course consisted of 28 days over which temozolomide was orally daily administered for 5 days (150 to 200 mg/m$^2$, once daily) followed by 23 days off treatment and the WT1 peptide vaccine was administered (3 mg, once weekly) for 4 weeks from the start of the administration of temozolomide. Therapy was discontinued in patient 6. As a result, the survival of all patients was prolonged, and PFS (progression-free survival) was 80 weeks or more in 5 of the 6 patients and 100 weeks or more in 4 patients.

TABLE 6

| Case | Age/Sex | Disease Name | Response | PFS (weeks) | OS (weeks) |
|---|---|---|---|---|---|
| 1 | 42/Male | Glioblastoma | CR | >135.1 | >135.1 |
| 2 | 55/Female | Glioblastoma | CR | >120.5 | >120.5 |
| 3 | 48/Male | Anaplastic Astrocytoma | CR | >115.2 | >115.2 |
| 4 | 41/Male | Glioblastoma | CR | >106.9 | >106.9 |
| 5 | 45/Male | Glioblastoma | CR | >83.5 | >83.5 |
| 6 | 60/Male | Glioblastoma | PD | 12.0 | >85.3 |

PFS: Progression-free survival
OS: Total survival

A comparison is shown in FIG. 1 between the total survival of patients given only radiation therapy or only a combination therapy of radiation therapy and temozolomide as reported in N. Engl. J. Med., 2005; 352: 987□996 (incorporated herein by reference) and the total survival of the patients given the combination therapy of the WT1 peptide vaccine of the present invention and temozolomide.

These results show that an excellent clinical effect is obtained by the combined use of the WT1 peptide vaccine therapy and chemotherapy with temozolomide.

Sequence Listing Free Text

SEQ ID NO. 2: Synthetic Peptide
SEQ ID NO. 3: Synthetic Peptide
SEQ ID NO. 4: Synthetic Peptide
SEQ ID NO. 5: Synthetic Peptide

The invention claimed is:

1. A method for treating a WT-1-expressing cancer, comprising administering therapeutically effective doses of a WT1 peptide and temozolomide to a human patient after radiation therapy in need thereof, wherein the WT1 peptide is (SEQ ID NO:6)

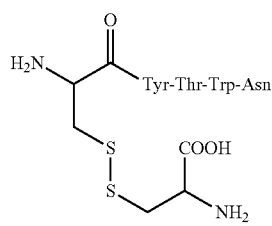

Tyr-Thr-Trp-Asn-Gln-Met-Asn-Leu-OH.

2. The method according to claim 1, wherein the cancer is glioma.

3. The method according to claim 1, wherein the WT1 peptide and temozolomide are administered to the human patient after extirpative surgery for tumor.

4. The method according to claim 1, wherein the WT1 peptide and temozolomide are administered to the human patient after a combination therapy of radiation therapy and temozolomide.

* * * * *